(12) United States Patent
McLaren et al.

(10) Patent No.: US 9,885,056 B2
(45) Date of Patent: Feb. 6, 2018

(54) PLANTS HAVING ENHANCED YIELD-RELATED TRAITS AND METHODS OF MAKING THEM

(71) Applicant: Iowa Corn Promotion Board, Johnston, IA (US)

(72) Inventors: James McLaren, Chesterfield, MO (US); Jagdeep Kaur, St. Louis, MO (US); David Ertl, Waukee, IA (US); Douglas Bryant, Vista, CA (US); Bala Venkata, St. Louis, MO (US)

(73) Assignee: Iowa Corn Promotion Board, Johnston, IA (US)

( * ) Notice: Subject to any disclaimer, the term of this patent is extended or adjusted under 35 U.S.C. 154(b) by 15 days.

(21) Appl. No.: 15/191,169

(22) Filed: Jun. 23, 2016

(65) Prior Publication Data

US 2017/0081677 A1 Mar. 23, 2017

Related U.S. Application Data

(60) Provisional application No. 62/183,322, filed on Jun. 23, 2015.

(51) Int. Cl.
| | |
|---|---|
| *A01H 5/00* | (2006.01) |
| *C12N 15/82* | (2006.01) |
| *C12Q 1/68* | (2006.01) |
| *C07K 14/415* | (2006.01) |

(52) U.S. Cl.
CPC ........ *C12N 15/8261* (2013.01); *C07K 14/415* (2013.01); *C12N 15/8227* (2013.01); *C12N 15/8241* (2013.01); *C12N 15/8271* (2013.01); *C12N 15/8279* (2013.01); *C12Q 1/68* (2013.01)

(58) Field of Classification Search
None
See application file for complete search history.

(56) References Cited

U.S. PATENT DOCUMENTS

| | | |
|---|---|---|
| 5,420,034 A | 5/1995 | Kridl et al. |
| 6,376,749 B1 | 4/2002 | Broglie et al. |
| 7,622,637 B2 | 11/2009 | Abbitt |
| 8,916,377 B2 | 12/2014 | Diehn et al. |
| 9,243,258 B2 | 1/2016 | Crow et al. |
| 2001/0047525 A1 | 11/2001 | Bruce et al. |

FOREIGN PATENT DOCUMENTS

| | | |
|---|---|---|
| EP | 3130675 A1 | 2/2017 |
| WO | 201025360 A1 | 2/2017 |

OTHER PUBLICATIONS

Wilson., NCBI, GenBank, Sequence Accession No. AC196768, Published Sep. 23, 2013.*
Sidorov et al., "Agrobacterium-mediated transformation of seedling-derived maize callus", "Genetic Transformation and Hybridization", Jan. 1, 2005, Publisher: Plant Cell Rep.
Furtado et al., "Analysis of promoters in transgenic barley and wheat", "Plant Biotechnology Journal", Jan. 1, 2009, pp. 240-253, vol. 7, Publisher: The Authors Journal Compilation.
Debodt et al., "CORNET 2.0: integrating plant coexpression, proteinprotein interactions, regulatory interactions, gene associations and functional annotations", Jan. 1, 2012, pp. 707-720, vol. 195, Publisher: New Phytologist.
Nusinow et al., "The ELF4-ELF3-LUX Complex Links the Circadian Clock to Diurnal Control of Hypocotyl Growth", "Nature.", Jan. 1, 2012, pp. 398-402, vol. 175, No. 7356, Publisher: HHS Public Access.
Curtis et al., "A Gateway Cloning Vector Set for High-Throughput Functional Analysis of Genes in Planta", "Breakthrough Technologies", Jan. 1, 2003, vol. 133, Publisher: Amiercan Society of Plant Biologists.
Sekhon et al., "Genome-wide atlas of transcription during maize development", "The Plant Journal", Jan. 1, 2011, pp. 553-563, vol. 66, Publisher: Society for Experimental Biology.
Lopez et al., "Characterization in maize of ZmTIP2-3, a root-specific tonoplast in trinisic protein exhibiting aquaporin activity", Feb. 1, 2004, pp. 539-541, vol. 55, No. 396.
Goodstein et al., "Phytozome: a comparative platform for green plant genomics", "Nucleic Acids Research", Jan. 1, 2012, vol. 40, Publisher: Oxford University Press.
Hajdukiewicz et al., "The small, versatile pPZP family of Agrobacterium binary vectors for plant transformation", "Plant Molecular Biology", Jan. 1, 1994, pp. 989-994, vol. 25, Publisher: Kulwer Academic Publishers.

* cited by examiner

*Primary Examiner* — Vinod Kumar
(74) *Attorney, Agent, or Firm* — Davis, Brown, Koehn, Shors & Roberts, P.C.; Mathew W. Coryell

(57) ABSTRACT

Methods and compositions for enhancing yield-related traits in plants by introducing and expressing in a plant a nucleic acid operably linked to a root-specific promoter, ICprom3.

20 Claims, 4 Drawing Sheets

PLANTS HAVING ENHANCED YIELD-RELATED TRAITS AND METHODS OF MAKING THEM

CROSS-REFERENCE TO RELATED APPLICATION(S)

This application claims priority to U.S. Provisional Application No. 62/183,322 that was filed on Jun. 23, 2015. The entire content of this provisional application is hereby incorporated herein by reference.

BACKGROUND OF THE INVENTION

Genetic transformation requires that the 5' end of the heterologous transgene is operably connected to a relevant promoter, in order to facilitate expression. Promoters are typically a region of nucleotide sequence located upstream of the 5' end of coding sequence and provide a binding site for RNA polymerase and any required transcription factors, thereby enabling the initiation of transcription.

Many promoters are constitutive and operate in multiple tissues in the plant. In cases where the object is to express the transgene in a particular tissue, then a tissue specific promoter is required. Seed, and even embryo or endosperm, specific promoters are known and have been used to express genes in seed, grain, and parts thereof (e.g. Abbitt, 2009; Broglie et al., 2002; Furtado et al., 2009; Kridl and Knauf 1995). In the case where genes are primarily or entirely expressed in the roots, a root specific promoter can provide control of gene expression is a desirable manner. Without intending to be limited, examples where root specific expression can provide valuable benefits include manipulating root size and structure; altering geotropism; drought tolerance and water relations; salt tolerance; pH control and buffering with the environment; controlling exudates; signal interactions with the soil microbiome; lowering biotic and abiotic stresses; endogenous hormone control; improving nutrient acquisition; altering root storage capacity; root lodging; disease control; insect control; nematode control; fungal control; microbial control; viral control; phytoremediation. Thus, there are many potentially valuable benefits from having strong specific root promoters.

A requirement arose for a root specific promoter (RSP). Some work has been done to design root specific promoters based on particular elements, but that approach has now been abandoned (Bruce and Niu, 2001). Accordingly, there is a need in the art for novel plant promoter sequences to efficiently drive expression of sequences of interest in tissues-specific basis, and particularly, in a root-specific basis.

BRIEF SUMMARY OF THE INVENTION

Disclosed herein is a recombinant DNA molecule comprising a promoter, the comprising the nucleotide sequence set forth in SEQ ID NO: 1, or a complement thereof, and a heterologous nucleotide sequence of interest, operably linked to the promoter, wherein promoter facilitates transcription of the nucleotide sequence of interest in a plant cell. In certain aspects, the recombinant DNA molecule is an expression cassette.

Further disclosed herein is are methods for expressing a nucleotide sequence of interest in a plant or a plant cell which comprise introducing into the plant or the plant cell an expression cassette comprising a promoter operably linked to the heterologous nucleotide sequence of interest, wherein the promoter comprises the sequence set forth in SEQ ID NO: 1, and wherein the promoter facilitates transcription in the plant. In certain aspects, the expression cassette further comprises a nucleotide sequence set forth in SEQ ID NO: 2.

Further disclosed herein is a method for inducing root-specific expression of a nucleotide sequence of interest in a plant comprising: introducing into a plant cell an expression cassette and regenerating a plant from the plant cell, the plant having stably incorporated into its genome the expression cassette, the expression cassette comprising a promoter operably linked to a heterologous nucleotide sequence of interest, wherein the promoter comprises a nucleotide sequence comprising the sequence set forth in SEQ ID NO: 1. In certain embodiments, The expression cassette further comprises a nucleotide sequence set forth in SEQ ID NO: 2. In further embodiments, the root-specific expression of the nucleotide sequence of interest results in enhanced yield-related traits in the plant relative to a wild-type plant. In still further embodiments, the enhanced yield-related traits are enhanced under conditions of biotic or abiotic stress. In yet further embodiments, the yield-related traits comprise: increased seed yield, increased biomass, improved protection against pests and diseases, and/or enhanced resource use efficiency.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figures 1, 2, 3:
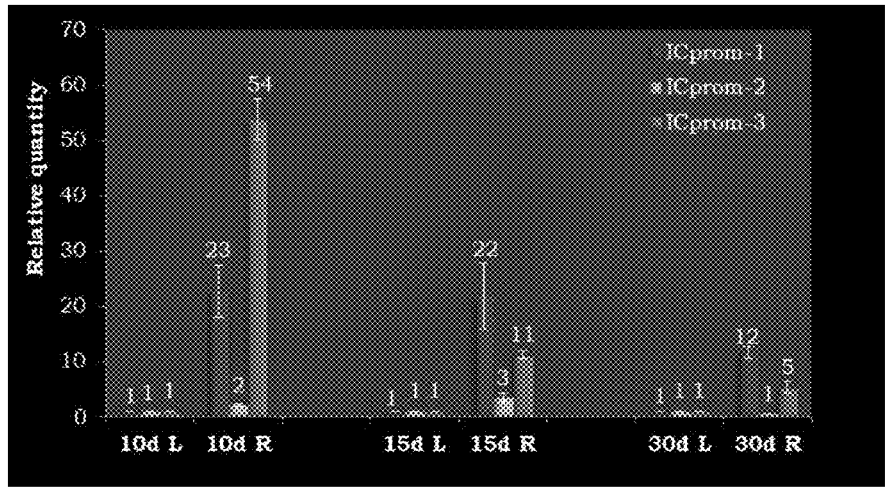
FIG. 1 is a chart of the quantitative RT-PCR analysis of promoter activity of promoter candidates ICprom1, ICprom2 and ICprom3 in different tissue of B73; the relative quantity was normalized to the reference gene GRMZM2G080603; error bars represent SE of three technical replicates; d=days after planting; L=leaf; R=root.
FIG. 2 shows SEQ ID NO. 3 and is a table of the nucleotide sequence of ICprom3 as determined using Genomatix® software; the restriction enzyme sited HindIII (5' end) and KpnI (3' end) were added for cloning before synthesis.
FIG. 3 shows SEQ ID NO. 4 and is a table of the nucleotide sequences of ICpromU3 as determined using 3' RACE; the restriction enzyme sites AscI (5' end) and PstI (3' end) were added for cloning before synthesis.

All publications mentioned herein are incorporated herein by reference to disclose and describe the methods and/or materials in connection with which the publications are cited. The publications discussed herein are provided solely for their disclosure prior to the filing date of the present application.

The following definitions and methods are provided to better define the invention and to guide those of ordinary skill in the art in the practice of the present invention. Unless otherwise noted, terms are to be understood according to conventional usage by those of ordinary skill in the relevant art.

As used herein, "enhanced yield-related traits" means any trait that tends to increase biomass (weight) of one or more parts of a plant, which may include aboveground (harvestable) parts and/or (harvestable) parts below ground. In particular, such harvestable parts are seeds, and performance of the methods or use of the composition disclosed herein results in plants having increased seed yield relative to the seed yield of control plants.

As used in this application, the term "resource" refers to all plant nutrients and plant functionalities or interactions that have an effect on plant nutrients, including but not limited to water, nitrogen, sunlight, carbon dioxide, phosphorus, minerals, carbon and microbial interactions.

As used herein, "expression" refers to the transcription and stable accumulation of mRNA. Expression may also refer to the production of protein.

As used herein, "expression cassette" means a DNA sequence capable of directing expression of a particular nucleotide sequence in an appropriate host cell, comprising a promoter operably linked to the nucleotide sequence of interest which is operably linked to termination signals and/or a 3' untranslated region (UTR). It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components.

As used herein, a "heterologous nucleotide sequence" or "heterologous nucleotide sequence of interest" is a sequence that is not naturally occurring with the promoter sequence of the invention. While this nucleotide sequence is heterologous to the promoter sequence, it may be homologous, or native, or heterologous, or foreign, to the plant host.

As used herein, the term "root-specific expression," means that expression of the heterologous nucleotide sequence is most abundant in the root or a root part, including, for example, the root cap, apical meristem, protoderm, ground meristem, procambium, endodermis, cortex, vascular cortex, epidermis, and the like. While some level of expression of the heterologous nucleotide sequence may occur in other plant tissue types, expression occurs most abundantly in the root or root part, including primary, lateral and adventitious roots.

As used herein, the term "operably linked" refers to a first DNA molecule joined to a second DNA molecule, wherein the first and second DNA molecules are arranged so that the first DNA molecule affects the function of the second DNA molecule. The two DNA molecules may or may not be part of a single contiguous DNA molecule and may or may not be adjacent. For example, a promoter is operably linked to a transcribable DNA molecule if the promoter is capable of affecting the transcription or translation of the transcribable DNA molecule.

As used herein, a "recombinant DNA molecule" is a DNA molecule comprising a combination of DNA molecules that would not naturally occur together without human intervention. For instance, a recombinant DNA molecule may be a DNA molecule that is comprised of at least two DNA molecules heterologous with respect to each other, a DNA molecule that comprises a DNA sequence that deviates from DNA sequences that exist in nature, or a DNA molecule that has been incorporated into a host cell's DNA by genetic transformation.

The present disclosure relates generally to plants having enhanced efficiency of resource use or yield-related traits and, more specifically, to root specific promoters for plants that, when transformed into plants, will assist in providing enhanced efficiency of resource use or yield-related traits.

Compositions disclosed herein include the nucleotide sequences for the promoter ICprom3 and fragments and variants thereof. In certain embodiments ICprom3 is comprised of the nucleotide sequence set forth in SEQ ID NO: 1. Fragments and variants of the disclosed promoter nucleotide sequences are also encompassed. In particular, fragments and variants of the sequence of SEQ ID NO: 1 may be used in the DNA constructs of the invention. As used herein, the term "fragment" refers to a portion of the nucleic acid sequence. Fragments of the promoter sequence may retain the biological activity of initiating transcription, more particularly driving transcription in a root-specific manner. Fragments of a nucleotide sequence for the promoter may range from at least about 20 nucleotides, about 50 nucleotides, about 100 nucleotides, and up to the full-length nucleotide sequence of the invention for the promoter. A person having ordinary skill in the art can readily ascertain promoter fragments having promoter activity by conducting expression assays.

As used herein, the term "variants" means substantially similar sequences. For nucleotide sequences, naturally occurring variants can be identified with the use of wellknown molecular biology techniques, such as, for example, with polymerase chain reaction (PCR) and hybridization techniques known in the art.

In specific embodiments, the promoter sequences of the invention are useful for expressing sequences of interest in a tissue-specific, particularly a root-specific manner. The nucleotide sequences of the invention also find use in the construction of expression vectors for subsequent expression of a heterologous nucleotide sequence in a plant of interest.

Disclosed herein is a recombinant DNA molecule comprising a promoter, the comprising the nucleotide sequence set forth in SEQ ID NO: 1, or a complement thereof, and a heterologous nucleotide sequence of interest, operably linked to the promoter, wherein promoter facilitates transcription of the nucleotide sequence of interest in a plant cell. In certain aspects, the recombinant DNA molecule is an expression cassette.

In certain embodiments, the recombinant DNA molecule further comprises a nucleotide sequence comprising the sequence set forth in SEQ ID NO: 2. In preferred embodiments, this sequence is downstream of the heterologous sequence of interest.

According to preferred embodiments, transformation of plants with the disclosed recombinant DNA molecule provides root specific expression of the heterologous sequence of interest. As will be appreciated by a person having skill in the art a variety of sequences would be beneficial to plant yield when expressed on a root-specific basis. For example, Bacillus thuringiensis endotoxin genes provide for protection against coleopteran insects by gut binding which enhances growth by protecting against root damage. See, e.g. U.S. Pat. No. 5,837,848. As described in U.S. Pat. No. 8,350,124, aquaporin genes expressed on a root-specific basis improves water retention. In certain embodiments, the heterologous sequence of interest encodes nematicidal polypeptides, which suppress or kill nematodes and thus enhance yield by protecting against root damage. See, e.g. U.S. Pat. No. 7,301,069. Furthermore, nitrogen transporter genes can be expressed on a root specific basis to facilitate nitrate uptake and thus enhance growth and nitrogen use efficiency. See, e.g. U.S. Pat. No. 7,982,093.

Further disclosed herein is are methods for expressing a nucleotide sequence of interest in a plant or a plant cell which comprise introducing into the plant or the plant cell an expression cassette comprising a promoter operably linked to the heterologous nucleotide sequence of interest, wherein the promoter comprises the sequence set forth in SEQ ID NO: 1, and wherein the promoter facilitates transcription in the plant. In certain aspects, the expression cassette further comprises a nucleotide sequence set forth in SEQ ID NO: 2.

Further disclosed herein is a method for inducing root-specific expression of a nucleotide sequence of interest in a plant comprising: introducing into a plant cell an expression cassette and regenerating a plant from the plant cell, the plant having stably incorporated into its genome the expression cassette, the expression cassette comprising a promoter operably linked to a heterologous nucleotide sequence of interest, wherein the promoter comprises a nucleotide sequence comprising the sequence set forth in SEQ ID NO: 1. In certain embodiments, The expression cassette further comprises a nucleotide sequence set forth in SEQ ID NO: 2. In further embodiments, the root-specific expression of the nucleotide sequence of interest results in enhanced yield-related traits in the plant relative to a wild-type plant. In still further embodiments, the enhanced yield-related traits are enhanced under conditions of biotic or abiotic stress. In yet further embodiments, the yield-related traits comprise: increased seed yield, increased biomass, improved protection against pests and diseases, and/or enhanced resource use efficiency.

According to certain embodiments, the plant is a sugarbeet, alfalfa, sugarcane, potato, soybean, rapeseed, cassava, maize, wheat, barley, millet, rye, triticale, sorghum, sunflower, rice, turf grass, cotton, peanut, tobacco, tomato, milo, oat, switchgrass, vegetable, fruits or tree. In preferred embodiments, the plant is maize.

EXPERIMENTAL EXAMPLES

An experimental plan was developed in order to generate a promoter with the desired target characteristics: (1) To be operative specifically in the root; (2) to have tight specificity to the root (not be leaky with operation in other tissues such as leaves); (3) to be relatively insensitive to environmental conditions, and to internal hormone signals; and (4) to facilitate expression in the roots, when operably linked to selected transgenes.

(A) Identifying Potential Specifically Root-Expressed Genes, and Promoters.

To identify such candidate genes, we began by obtaining all publically available tissue-specific RNA-seq data in maize from the NCBI short read archive (ncbi.nlm.nih.go-visra). Using the B73 genomic reference sequence, we used cufflinks to evaluate tissue-specific differentially expressed genes (cole-trapnelllab.github.io/cufflinks/tools/). Based on the results of these analyses we identified genes as root-specifically expressed if (1) the gene was expressed in root at a minimum of five fragments per kilobase of exon per million fragments mapped (FPKM) in the root, and (2) the gene was expressed at no greater than some minimal level (1%, 2%, 3%, 4%, or 5%) of its root expression in the next highly expressed tissue. Genes were then ranked by this expression ratio (root expression to next highest tissue expression) for further examination. A total of 184 genes were identified using this approach.

For each selected high priority gene its promoter sequence, defined as 500 to 1000 bp upstream of its transcription start site, was obtained and analyzed for known promoter motifs (e.g. TATA box) using available bioinformatic tools via genomatix (available at (togenomatix.de/) or the ExPASy portal (expasy.org).

(B) Shortlist the Candidates from Above List for Further Analysis.

The above dataset of 184 genes was further evaluated and the top priority candidates were selected using four different parameters.

The first criterion was to determine if any of the candidate genes, or their interacting partners, were associated with known genes in a relevant biosynthetic pathway. Using the data-mining tool called CORNET (De Bodt et al. 2012) for network correlation analysis, it was found that no potential associations existed.

The second criterion involved determining if the above genes, or their interacting partners, were responsive to the trait of interest (TOI). In order to tap into the robust Arabidopsis trait association data sets, we first identified the Arabidopsis orthologs of the above genes via the amino acid sequence search query in phytozome (Goodstein et al 2012). This criterion allowed the selection of 9 putative RSP candidates (Table 1). Three of the genes represented in Table 1 were each positively, negatively and non-responsive to the TOI. We also selected gene GRMZM2G146502 from the original list due to annotation as root cap periphery 2 protein. Another gene GRMZM2G125023 (ZmTIP2-3) that codes for a tonoplast intrinsic protein was identified through a literature search and was added to the shortlisted candidates list (Table 1).

TABLE 1

List of candidates shortlisted for further analysis.

| Gene | *Zea mays* gene ID | *Arabidopsis thaliana* ortholog gene ID |
|---|---|---|
| 1 | GRMZM2G023847 | AT5G20230 |
| 2 | GRMZM2G122018 | AT5G39150 |
| 3 | GRMZM2G133475 | AT5G05340 |
| 4 | GRMZM2G056908 | AT4g23400 |
| 5 | GRMZM2G477697 | AT2g10940 |
| 6 | GRMZM2G304442 | AT4g25780 |
| 7 | GRMZM2G112619 | AT4g25820 |
| 8 | GRMZM2G054115 | AT4g24670 |
| 9 | GRMZM2G132273 | AT3G58090 |
| 10 | GRMZM2G146502 | AT3G19430.1 |
| 11 | GRMZM2G125023 | AT4G17340 |

Genes 1-3 are positively responsive to TOI; Genes 4-6 are negatively responsive to TOI; Genes 7-9 are non-responsive to TOI; 
Gene GRMZM2G146502 is annotated as root cap periphery 2 protein; 
Gene GRMZM2G125023 is a tonoplast intrinsic protein.

The 11 top priority candidates (Table 1) were subsequently analyzed for the desired spatial kinetics. Using the Maize-EFP browser (Sekhon et al. 2011) it was shown that each was associated with root preferred expression.

The final criterion was based on evaluations to determine if any potential intellectual property issues were known.

The above analyses resulted in the selection of 3 three genes for validation studies: GRMZM2G112619, GRMZM2G146502 and GRMZM2G125023.

(C) Determine Gene Expression Level, to Check on Root Activity.

The 3 selected genes (proxies for RSP candidates), GRMZM2G146502 (in short, ICprom1g), GRMZM2G112619 (ICprom2g) and GRMZM2G125023 (ICprom3g) were evaluated for tissue specific expression using qRT-PCR. For this analysis, the maize inbred B73 was grown in the integrated plant growth facility under the growth regime of 80.6-84.2° F. day/night temperature, 30% minimum RH, 16 hour day length, in Turface® potting material (allows easy extraction of roots). Drip irrigation was set for 10 min, 3×/day with a drip rate of ½ gallon per hour. Leaf and root tissue (100 mg) from 10, 15 and 30 days old plants was collected in liquid nitrogen and stored at −80° C. freezer until further use. Total RNA was isolated from leaf and root tissue collected at various time points using RNeasy mini kit (Qiagen, Cat #74104) following the manufacturer's instructions. After quantification of RNA on a Nanodrop 2000 spectrophotometer (Thermo Scientific, Waltham, Mass., USA) 3 µg of total RNA was treated with DNaseI to remove DNA using Turbo DNA free kit (Ambion, Cat # AM1907). RNA was transcribed into cDNA using SuperScript III® first-strand synthesis system (Invitrogen, La Jolla, Calif., USA). The cDNA samples were quantified using the CFX-384 Real Time System (Bio-rad) using buffer containing of 1×Taq buffer, 1×SYBR Green, 10 nM fluorescein (Bio-rad), 0.1% (v/v) Tween 20, 5% (v/v) DMSO, 50 µg/ml BSA, 0.25 mM dNTPs, 250 nM primers and 1 U Taq DNA polymerase. The PCR conditions were initial denaturation at 95° C. for 3 mins, 40 cycles of 95° C. for 10 s, 55° C. for 10 s, 72° C. for 20 s (Nusinow et al. 2011). The glycine-rich RNA binding protein 2 gene from maize (GRMZM2G080603) was used as the normalization control (Sekhon et al. 2011). Primers were designed using Primer 3 and are listed in Table 2.

TABLE 2

Oligonucleotide sequences of the primers used for RT-qPCR study.

| Primer | Sequence (5'-3') |
|---|---|
| GRMZM2G125023 F | TACGTCACCCACGGACAG |
| GRMZM2G125023 R | GCCGTGCGTCGGGATAGC |
| GRMZM2G146502 F | CGACGAAAGCACGAGAGTTA |
| GRMZM2G146502 R | GCCTTATTGCGGTGTGAATG |
| GRMZM2G112619 F | GATGGCTCTCCTCCTTGTTG |
| GRMZM2G112619 R | TCGTAAACCTGGCGTTCTG |
| GRMZM2G080603 F | AGGTCCTCGAGTCCAAG |
| GRMZM2G080603 R | CTCCTTGCCGTTCATGC |

Quantitative RT-PCR data (analyzed using ΔΔCt method) indicated that ICprom1g showed 23-, 22- and 12-fold more expression in root at 10 d, 15 d and 21 d, respectively, compared to leaf at same time points. ICprom2g showed 2- and 3-fold expression at 10 d and 15 d but expression decreased at 21 d. At 10 d, ICprom3g expression in root tissue was 54-fold higher compared to leaf, and 22- and 12-fold higher at 15 d and 21 d, respectively, compared to leaf tissue (FIG. 1).

Based on these data, the upstream promoters of ICprom1g and ICprom3g were selected to build promoter-reporter constructs for determination of expression activity in various tissue types.

(D) Determining the Expression Activity of Top Candidates in Various Tissues.

From the selected genes, ICprom1g and ICprom3g, the 5' promoter lengths of 601 bp and 637 bp, respectively, were calculated based on Gene2Promoter analysis computed with Genomatix® software. Using the 3' RACE system for rapid amplification of cDNA ends (Invitrogen, Cat #18373-019) we determined the in planta length of 3' UTRs for ICprom1g and ICprom3g to be 201 bp and 230 bp, respectively.

The promoter candidates ICprom1 and ICprom3 and their respective 3' UTRs-ICpromU1 and ICpromU3 were synthesized (under contract at GenScript) with appropriate RE sites added. A reporter gene, herein termed GOI, was also synthesized at Genscript. The promoter candidates ICprom1 and ICprom3 were fused with GOI using HindIII and KpnI sites. ICpromU1 and ICpromU3 3' UTRs were ligated to the promoter-GOI using the AscI and PstI sites. The fusion fragment ICprom1/GOI/ICpromU1 and ICprom3/GOI/ICpromU3 were cloned, using the HindIII and PstI sites, into the binary vector pPZP212 (Hajdukiewicz et al., 1994) containing nptII as the plant selectable marker.

The pPZP212 vectors containing the promoter candidate-GOI constructs were then transferred to *Agrobacterium tumefaciens* strain EHA101 for maize transformation.

Figure 4:
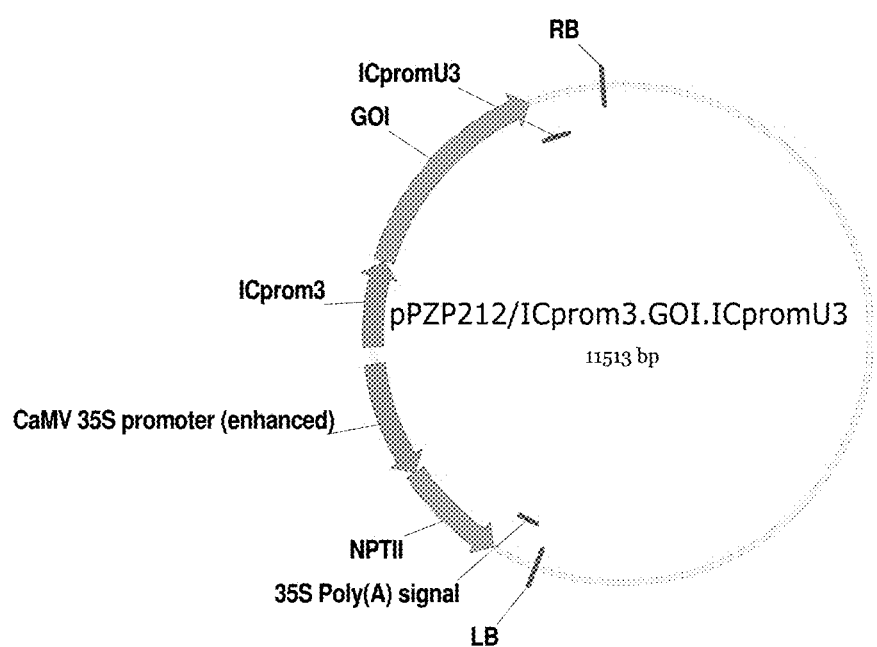
FIG. 4 is a map of pPZP212 Agrobacterium binary vector carrying ICprom3/GOI/ICpromU3 expression cassette; a 3' UTR acting as an enhancer element; neomycin phosphotransferase (nptII) is the plant selectable marker.

Initial evaluations of the candidate RSPs, in transgenic plants, indicated that ICprom1 did not have consistent results and was not clearly root-specific while ICprom3 was a consistent and superior RSP. Consequently, the description of the reduction to practice and further evaluations will be for ICprom3. FIG. 2 shows the synthesized sequence of ICprom3 and FIG. 3 shows the respective 3' UTR region, each with the RE sites added. FIG. 4 is a map of the transformation vector for ICprom3/GOI/ICpromU3.

To generate transgenic maize, immature embryos of the maize inbred line H99 were used following the protocol as described in Sidorov et al., 2005. All plants were grown in the greenhouse as described previously. $T_0$ plants were crossed to the inbred line B73 to generate $T_1$ plants for evaluations.

Maize $T_1$ plants carrying the ICprom3/GOI/ICpromU3 were harvested and the expression of the GOI in leaves and roots was analyzed via RT-PCR and quantitative RT-PCR, as described previously.

Figure 5:
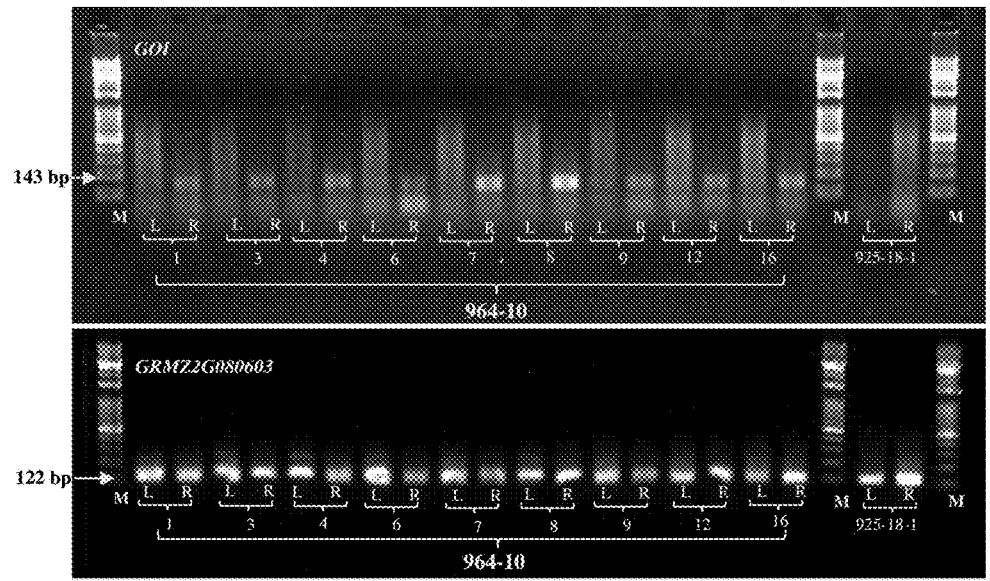
FIG. 5 is an agarose gel of RT-PCR in 10 day old leaf (L) and root (R) tissues of pPZP212/ICprom3:GOI:ICpromU3 derived stable transgenic $T_1$ maize event 964-10. Data from nine individual families i.e., 964-10-1, -3, -4, -6, -7, -8, -9, -12 and -16 are presented. Leaf and root tissue from empty vector maize $T_1$ family line 925-18-1 was used as negative control. Panel A—GOI (gene of interest) data; panel B—reference gene GRMZ2G080603 data. M—VersaLadder™ (100-10000 bp) from Gold Bio.
Figure 6:
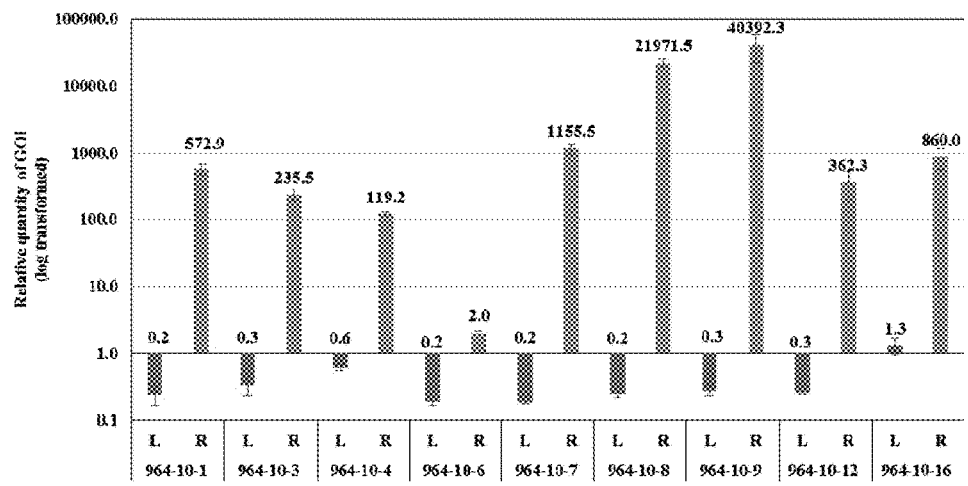
FIG. 6 is a chart of the quantitative RT-PCR analyses of the GOI in 10 day old leaf (L, in green) and root (R, in blue) tissues of pPZP212/ICprom3:GOI:ICpromU3 derived stable transgenic T₁ maize event 964-10. Data from nine individual families i.e., 964-10-1, -3, -4, -6, -7, -8, -9, -12 and -16 are presented. The expression was normalized to reference gene GRMZM2G080603, and relative quantity is calculated from empty vector control L and R tissue set at 1. Error bars represent standard errors of three replicates (±SE).

FIG. 5 shows the RT-PCR results for leaves and roots for the GOI and an endogenous reference gene (GRMZ2G080603), for 9 individual families from the transgenic event 964-10. The reference gene data indicates expression in leaves and roots while the GOI expression is more evident in the roots. Quantitative RT-PCR results (FIG. 6) show that, relative to the reference gene, the GOI is expressed several fold more in the roots and not in the leaves.

Figure 7:
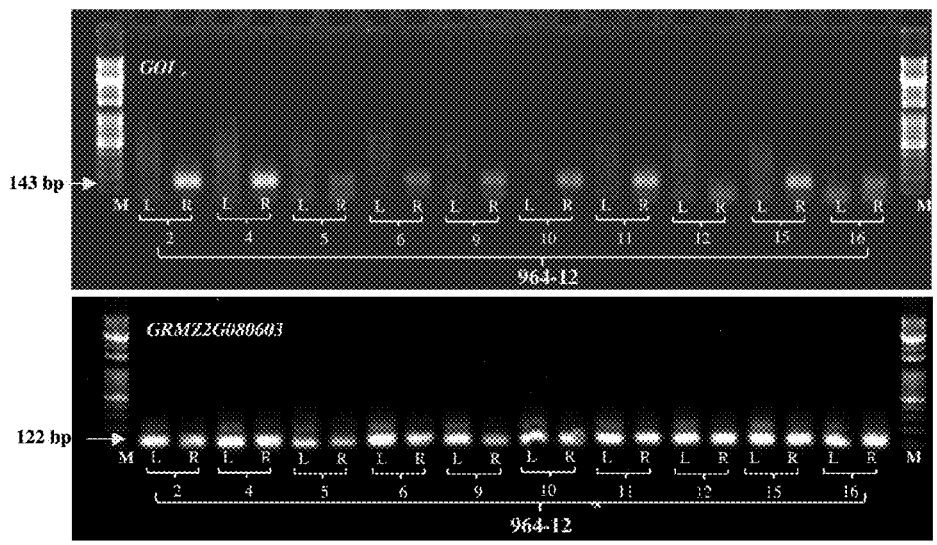
FIG. 7 is an agarose gel of RT-PCR in 10 day old leaf (L) and root (R) tissues of pPZP212/ICprom3:GOI:ICpromU3 derived stable transgenic T₁ maize event 964-12. Data from ten individual families i.e., 964-12-2, -4, -5, -6, -9, -10, -11, -12, -15 and -16 are presented. Leaf and root tissue from empty vector maize T₁ family line 925-18-1 was used as negative control (data not shown). Panel A—GOI data; panel B—reference gene GRMZ2G080603 data. M—VersaLadder™ (100-10000 bp) from Gold Bio.
Figure 8:
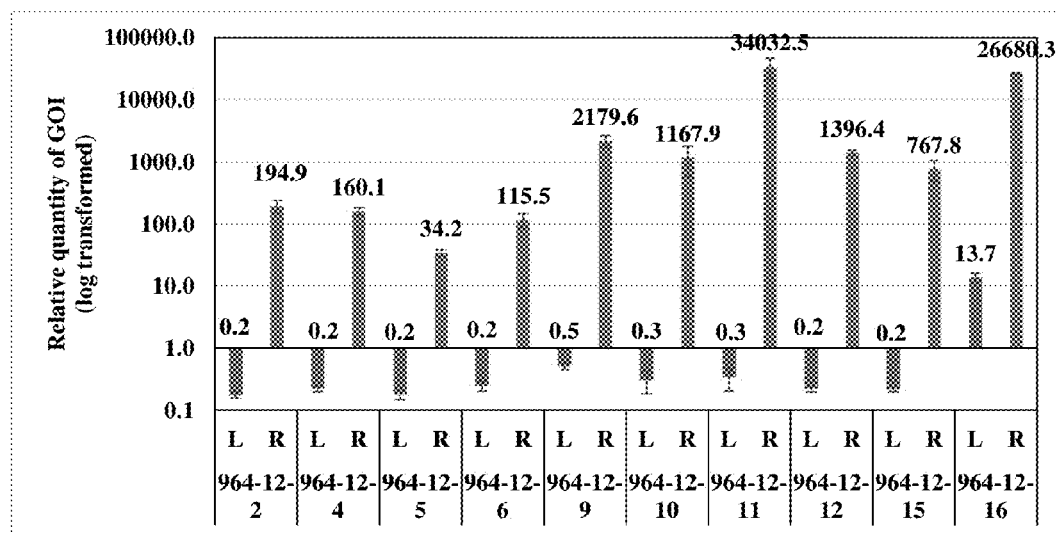
FIG. 8 is a chart of the quantitative RT-PCR analyses of GOI in 10 day old leaf (L, in green) and root (R, in blue) tissues of PZP212/ICprom3:GOI:ICpromU3 derived stable transgenic T₁ maize event 964-12. Data from ten individual families i.e., 964-12-2, -4, -5, -6, -9, -10, -11, -12, -15 and -16 are presented. The expression was normalized to reference gene GRMZM2G080603, and relative quantity is calculated from empty vector control L and R tissue set at 1. Error bars represent standard errors of three replicates (±SE).

FIG. 7 and FIG. 8, respectively, confirm the same relative results as above for another independent transgenic event, 964-12, with the ICprom3/GOI/ICprom3 construct.

The data provided above demonstrate that ICprom3 is a strong root specific promoter.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

REFERENCES

Abbitt S E. (2009). Seed-preferred regulatory elements. U.S. Pat. No. 7,622,637.

Broglie K E., Hubbard N L., Klein™., and Lightner J E. (2002) Starches via modification of expression of starch biosynthetic enzyme genes. U.S. Pat. No. 6,376,749.

Bruce W B. and Niu X. (2001). Novel root-preferred promoter elements and methods of use. USPTO application 20010047525. Now abandoned.

Curtis M D, Grossniklaus U. (2003). A Gateway Cloning Vector Set for High-Throughput Functional Analysis of Genes in Planta. Plant Physiology, 133(2): 462-469.

De Bodt S., Hollunder J., Nelissen H., Meulemeester N., Inze' D. (2012). CORNET 2.0: integrating plant coexpression, protein-protein interactions, regulatory interactions, gene associations and functional annotations. *New Phytol.* 195:707-20.

Furtado A., Henry R J. and Pellegrineschi A. (2009). Analysis of promoters in transgenic barley and wheat. Plant Biotech Journal, 7, 240-253.

Goodstein D M., Shu S., Howson R., Neupane R., Hayes R D., Fazo J., et al. Phytozome: a comparative platform for green plant genomics. Nucleic Acids Res. 2012; 40: D1178-D1186.

Hajdukiewicz P., Svab Z. and Maliga P. (1994). The small, versatile pPZP family of *Agrobacterium* binary vectors for plant transformation. Plant Molecular Biology, 25 (6): 989-994.

Kridl J C. and Knauf V C. (1995). Seed-specific transcriptional regulation. U.S. Pat. No. 5,420,034.

Nusinow D A., Helfer A., Hamilton E E., et al. (2011). The ELF4-ELF3-LUX Complex Links the Circadian Clock to Diurnal Control of Hypocotyl Growth. Nature, 475 (7356): 398-402.

Sekhon R S., Lin H., Childs K L., Hansey C N., Buell C R., de Leon N. and Kaeppler S M. (2011). Genome-wide atlas of transcription during maize development. The Plant Journal, 66: 553-563.

Sidorov V, Gilbertson L, Addae P and Duncan D. (2005). *Agrobacterium* mediated transformation of seedling-derived maize callus. Plant Cell Rep. 25, 320-328.

---

SEQUENCE LISTING

SEQ ID NO: 1

```
  1  GCTTGTTTTT CCTCAGTTTG GTTCAAACGT CCGTATTACT ATAGTCGTGT TACTATAGTT
 61  GTGTATGTGC ATAATTGTTT TATTTTCATT TTTTTACCGC CTAAAAAATT TCCTGGCAAA
121  CAAAGCTCTT GTCACCCCTC CTAAAAAAAT AGATCAGTAG ATACACGGTA GAAATAAAGG
181  ATCAATTCAC ATATCACACC GCGCCGCCAT TGATTGTTT AGGCAAGAGA TATCACTGTA
241  TGCTCCAAGG TCTTGTTCCT CCTCGCTGTC TCATGGCGTA TCCTAACGTG CGTGTCTCGA
301  CCTGAAGAAC CACAACTACA CATCAATTCA GCGAGTTAGG GCGGTTGGTC GACCAGTGTC
361  AGCCACAAAA CGCGGCCAAA ATTTAAATTA TCAATCATGT GGTGATCATT GCGCACCGCC
421  CATAGTATTG TAAGGCACAT CCGAGGCAAG GCAGCGCATT ATGACGTGTA TTTAAGGAGA
481  CTAAGCTGAA GGAACTCTCG CATCAGCGGC CTGATAAGCT ATAGCCATCT TCTTCTCTGA
541  ATTCCAGTCC AAGGGCCGGA ATACCGTCAG AGGGAGTGGG AGAGGGGGG AAAAAAGATG
601  GTGAAGCTCG CATTTGGAAG CTTTCGCGAC TCTTTGA
```

SEQ ID NO: 2

```
AAGTCCGGATGAGCTAGCCCGATCGATCCGTCTGTGTTGATTTCACCATCGTCGTCGTCGTGTCATCTGG
CGCTTCGTGCTGTGATCATGTTTTGTCCTGTTTGCATTTCCCAACGTCTGGTTTTCATTTCCATTCACCA
ACGGTGCCAAGATGCCGTAAGCAAGCGAGAGAAGTGTTCGGTCTGTATCTGTATAAATGCAATGCACAGT
TCGGCGTTTCCATGAACGAA
```

We claim:

1. A method for expressing a nucleotide sequence of interest in a plant or a plant cell comprising introducing into the plant or the plant cell an expression cassette comprising a promoter operably linked to a heterologous nucleotide sequence of interest, wherein the promoter comprises the sequence set forth in SEQ ID NO: 1, and wherein the promoter facilitates transcription in the plant.

2. The method of claim 1, wherein the expression cassette further comprises the nucleotide sequence set forth in SEQ ID NO: 2.

3. A method for inducing root-specific expression of a nucleotide sequence of interest in a plant comprising: introducing into a plant cell an expression cassette and regenerating a plant from the plant cell, the plant having stably incorporated into its genome the expression cassette, the expression cassette comprising a promoter operably linked to a heterologous nucleotide sequence of interest, and wherein the promoter comprises a nucleotide sequence comprising the sequence set forth in SEQ ID NO: 1.

4. The method of claim 3, wherein the expression cassette further comprises the nucleotide sequence set forth in SEQ ID NO: 2.

5. The method of claim 3, wherein root-specific expression of the nucleotide sequence of interest results in enhanced yield-related traits in the plant relative to a wild-type plant.

6. The method of claim 5, wherein the enhanced yield-related traits are enhanced under conditions of biotic or abiotic stress.

7. The method of claim 5, wherein the yield-related traits comprise: increased seed yield, increased biomass, improved protection against pests and diseases or enhanced resource use efficiency.

8. The method of claim 3, wherein the plant is a sugarbeet, alfalfa, sugarcane, potato, soybean, rapeseed, cassava, maize, wheat, barley, millet, rye, triticale, sorghum, sunflower, rice, turf grass, cotton, peanut, tobacco, tomato, milo, oat, switchgrass, vegetable, fruits or tree.

9. An expression cassette comprising:
   a. a promoter comprising the nucleotide sequence set forth in SEQ ID NO: 1; and
   b. a heterologous nucleotide sequence of interest, operably linked to the promoter, and wherein promoter facilitates transcription of the nucleotide sequence of interest in a plant cell.

10. The expression cassette of claim 9, further comprising the nucleotide sequence set forth in SEQ ID NO: 2.

11. A recombinant vector comprising the expression cassette of claim 9.

12. The recombinant vector of claim 11, wherein the vector is a plasmid.

13. A recombinant vector comprising the expression cassette of claim 10.

14. The recombinant vector of claim 13, wherein the vector is a plasmid.

15. A plant, plant part or plant cell, transformed with the expression cassette of claim 9.

16. A plant transformed with the expression cassette of claim 9, and wherein the heterologous sequence of interest is expressed in a root-specific manner.

17. The plant of claim 15, wherein the plant is a sugarbeet, alfalfa, sugarcane, potato, soybean, rapeseed, cassava, maize, wheat, barley, millet, rye, triticale, sorghum, sunflower, rice, turf grass, cotton, peanut, tobacco, tomato, milo, oat, switchgrass, vegetable, fruits or tree.

18. A harvestable part of the plant according to claim 15, wherein the harvestable part is a seed, and wherein the seed comprises the expression cassette.

19. The plant of claim 15, wherein the plant has enhanced yield-related traits comprising increased seed yield, increased biomass, improved protection against pests and diseases or enhanced resource use efficiency, relative to wild-type plants.

20. The plant of claim 15, wherein the enhanced yield-related traits are enhanced under conditions of biotic or abiotic stress.

* * * * *

SEQUENCE LISTING

<160> NUMBER OF SEQ ID NOS: 4

<210> SEQ ID NO 1
<211> LENGTH: 637
<212> TYPE: DNA
<213> ORGANISM: Artificial
<220> FEATURE:
<223> OTHER INFORMATION: Synthetic

<400> SEQUENCE: 1

| | | | | | |
|---|---|---|---|---|---|
| gcttgttttt | cctcagtttg | gttcaaacgt | ccgtattact | atagtcgtgt | tactatagtt | 60 |
| gtgtatgtgc | ataattgttt | tattttcatt | tttttaccgc | ctaaaaaatt | tcctggcaaa | 120 |
| caaagctctt | gtcaccccct | ctaaaaaaat | agatcagtag | atacacggta | gaaataaagg | 180 |
| atcaattcac | atatcacacc | gcgccgccat | tgatttgttt | aggcaagaga | tatcactgta | 240 |
| tgctccaagg | tcttgttcct | cctcgctgtc | tcatggcgta | tcctaacgtg | cgtgtctcga | 300 |
| cctgaagaac | cacaactaca | catcaattca | gcgagttagg | gcggttggtc | gaccagtgtc | 360 |
| agccacaaaa | cgcggccaaa | atttaaatta | tcaatcatgt | ggtgatcatt | gcgcaccgcc | 420 |
| catagtattg | taaggcacat | ccgaggcaag | gcagcgcatt | atgacgtgta | tttaaggaga | 480 |
| ctaagctgaa | ggaactctcg | catcagcggc | ctgataagct | atagccatct | tcttctctga | 540 |
| attccagtcc | aagggccgga | ataccgtcag | agggagtggg | agagggggg | aaaaagatg | 600 |
| gtgaagctcg | catttggaag | ctttcgcgac | tctttga | | | 637 |

<210> SEQ ID NO 2
<211> LENGTH: 230
<212> TYPE: DNA
<213> ORGANISM: Artificial
<220> FEATURE:
<223> OTHER INFORMATION: Synthetic

<400> SEQUENCE: 2

| | | | | | |
|---|---|---|---|---|---|
| aagtccggat | gagctagccc | gatcgatccg | tctgtgttga | tttcaccatc | gtcgtcgtcg | 60 |
| tgtcatctgg | cgcttcgtgc | tgtgatcatg | ttttgtcctg | tttgcatttc | ccaacgtctg | 120 |
| gttttcattt | ccattcacca | acggtgccaa | gatgccgtaa | gcaagcgaga | gaagtgttcg | 180 |
| gtctgtatct | gtataaatgc | aatgcacagt | tcggcgtttc | catgaacgaa | | 230 |

<210> SEQ ID NO 3
<211> LENGTH: 649
<212> TYPE: DNA
<213> ORGANISM: Artificial Sequence
<220> FEATURE:
<223> OTHER INFORMATION: Synthetic

<400> SEQUENCE: 3

| | | | | | |
|---|---|---|---|---|---|
| aagcttgctt | gttttcctc | agtttggttc | aaacgtccgt | attactatag | tcgtgttact | 60 |
| atagttgtgt | atgtgcataa | ttgttttatt | ttcattttt | taccgcctaa | aaatttcct | 120 |
| ggcaaacaaa | gctcttgtca | cccctcctaa | aaaatagat | cagtagatac | acggtagaaa | 180 |
| taaaggatca | attcacatat | cacaccgcgc | cgccattgat | ttgtttaggc | aagagatatc | 240 |
| actgtatgct | ccaaggtctt | gttcctcctc | gctgtctcat | ggcgtatcct | aacgtgcgtg | 300 |
| tctcgacctg | aagaaccaca | actacacatc | aattcagcga | gttagggcgg | ttggtcgacc | 360 |
| agtgtcagcc | acaaaacgcg | gccaaaattt | aaattatcaa | tcatgtggtg | atcattgcgc | 420 |
| accgccata | gtattgtaag | gcacatccga | ggcaaggcag | cgcattatga | cgtgtattta | 480 |
| aggagactaa | gctgaaggaa | ctctcgcatc | agcggcctga | taagctatag | ccatcttctt | 540 |

```
ctctgaattc cagtccaagg gccggaatac cgtcagaggg agtgggagag gggggggaaaa      600 aagatggtga agctcgcatt tggaagcttt cgcgactctt tgaggtacc                  649

<210> SEQ ID NO 4
<211> LENGTH: 244
<212> TYPE: DNA
<213> ORGANISM: Artificial Sequence
<220> FEATURE:
<223> OTHER INFORMATION: Synthetic

<400> SEQUENCE: 4
ggcgcgccaa gtccggatga gctagcccga tcgatccgtc tgtgttgatt tcaccatcgt       60
cgtcgtcgtg tcatctggcg cttcgtgctg tgatcatgtt ttgtcctgtt tgcatttccc      120
aacgtctggt tttcatttcc attcaccaac ggtgccaaga tgccgtaagc aagcgagaga      180
agtgttcggt ctgtatctgt ataaatgcaa tgcacagttc ggcgtttcca tgaacgaact      240
gcag                                                                  244
```